United States Patent

(12) United States Patent
Devance

(10) Patent No.: US 6,263,724 B1
(45) Date of Patent: Jul. 24, 2001

(54) GAS ANALYZING APPARATUS

(75) Inventor: Alain Devance, Ugine (FR)

(73) Assignee: Alcatel, Paris (FR)

( * ) Notice: Subject to any disclaimer, the term of this patent is extended or adjusted under 35 U.S.C. 154(b) by 0 days.

(21) Appl. No.: 09/284,206

(22) PCT Filed: Aug. 10, 1998

(86) PCT No.: PCT/FR98/01782

§ 371 Date: Jul. 8, 1999

§ 102(e) Date: Jul. 8, 1999

(87) PCT Pub. No.: WO99/08086

PCT Pub. Date: Feb. 18, 1999

(30) Foreign Application Priority Data

Aug. 11, 1997 (FR) .................................................. 97 10259

(51) Int. Cl.⁷ .................................................. G01M 3/04
(52) U.S. Cl. .................................................. 73/40.07; 73/1.06
(58) Field of Search .................................................. 73/40.7, 1.02, 73/1.03, 1.06

(56) References Cited

U.S. PATENT DOCUMENTS 4,680,956 * 7/1987 Huszczuk .............................. 73/1.05
4,797,784 * 1/1989 Grosse Bley .......................... 73/1.03
5,835,974 * 11/1998 Nagy ..................................... 73/1.06

FOREIGN PATENT DOCUMENTS

| 2 366 553 | 4/1978 | (FR) . |
| 2 606 878 | 5/1988 | (FR) . |
| 2 688 307 | 9/1993 | (FR) . |

OTHER PUBLICATIONS

B. Piégay: "Les Détecteures de fuites á hélium. Conception et étallonnage" Le Vide: Science, Technique et Applications., vol. 51, No. 278, Nov. 1995, FR, pp. 443–455, XP000557206.

J.C. Legras, et al.: "Létalonnage des fuites de rérence au BNM/L.N.E." Le Vide: Science, Technique et Applications., vol. 51, No. 278, Nov. 1995, FR, pp. 436–442, XP000557205.

* cited by examiner

Primary Examiner—Daniel S. Larkin
(74) Attorney, Agent, or Firm—Sughrue, Mion, Zinn, Macpeak & Seas, PLLC

(57) ABSTRACT

A gas analyzer comprising a pump unit and autocalibration means, characterized in that the gas analyzer is connected to a storage tank having a calibrated leak and filled with a mixture of n gases having different masses, and wherein the partial leakage flow of each of said n gases which through said calibrated leak is known.

8 Claims, 2 Drawing Sheets

GAS ANALYZING APPARATUS

BACKGROUND OF THE INVENTION

The invention concerns a gas analyser including a pump unit and autocalibration means.

The invention applies in particular to a gas analyser that is part of a tracer gas leak detector.

Tracer gas leak detectors generally include autocalibration means, i.e. means for calibrating the detector. To this end the device includes a container of tracer gas, generally helium, having a known and calibrated leakage rate.

The container is connected to the inlet of the detector by a valve which is opened during autocalibration. To enable calibration, the calibrated leakage flow is entered into an electronic circuit, for example using thumbwheels on the device, the electronic circuit adjusting the ionisation current of the gas analyser. The device carries a mass selector switch, generally selecting one of three separate possible masses, operating on the ion acceleration voltage. This is so even though the detector contains only one calibrated leakage container for a given gas.

Accordingly, if a tracer gas other than that in the calibrated leakage container inside the device is to be used, it is necessary to use a calibrated leakage cylinder of the other gas and to connect it to the inlet flange of the device and of course to open the device to set the calibrated leakage value of that cylinder on the thumbwheels. The mass selector switch must also be set to the position corresponding to the gas used.

When this has been done, the above parameters (ion acceleration voltage and ionisation current) are adjusted automatically during autocalibration so that the leak shown on the device corresponds to the calibrated leakage flow entered via the thumbwheels.

SUMMARY OF THE INVENTION

An aim of the present invention is therefore to propose a gas analyser equipped with means for automatically calibrating it in a very simple manner using a plurality of different gases.

An analyser of the above kind can be used directly to analyse a gas or as part of a leak detector that can be used with a plurality of different tracer gases by simplifying to the greatest possible degree the operations to be carried out when the tracer gas used is changed.

The invention therefore consists in a gas analyzer connected to a pump unit and including auto calibration means characterised in that it is connected to a storage tank having a calibrated leak and filled with a mixture of n gases having different masses and the leakage flow of each of said n gases which through said calibrated leak is known.

In an advantageous embodiment of the invention, the concentration of each of the n gases in the mixture is such that said partial leakage flow of each of the n gases through said calibrated leak is the same for all of them. This enables a single value of the leakage flow to be set that is valid for all the n gases.

BRIEF DESCRIPTION OF THE DRAWINGS

One embodiment of the invention will now be described with reference to the accompanying drawings, in which.

DETAILED DESCRIPTION OF THE INVENTION

Figure 1:
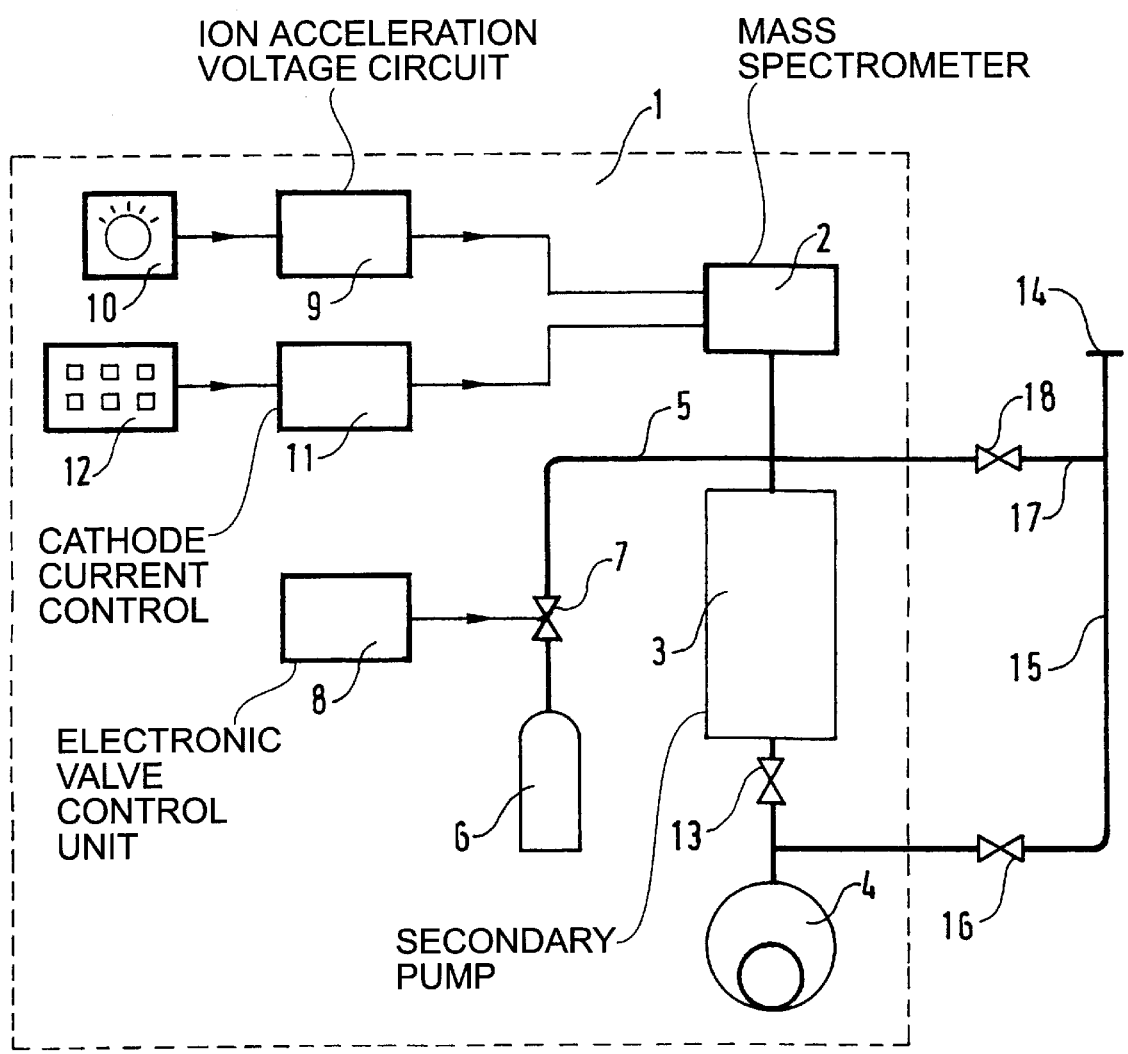
FIG. 1 is a diagram of a tracer gas leak detector including a gas analyser in accordance with the invention.

FIG. 1 shows a tracer gas leak detector using a gas analyser in accordance with the invention. The gas analyser, within the dashed line frame 1, comprises a mass spectrometer 2 with its pump unit, comprising a secondary pump 3 and a primary pump 4, and autocalibration means.

The autocalibration means include a storage tank 6 having a calibrated leak (for example a calibrated orifice). The storage tank is connected to the spectrometer 2 by a pipe 5 via a valve 7 controlled by an electronic automatic control circuit 8.

In accordance with the invention, the storage tank 6 is filled with a mixture of n gases with different masses (for example helium 4, helium 3, and hydrogen). The partial leakage flow of each of the n gases through the calibrated leak is obviously known.

The concentration of each of the n gases in the mixture is preferably chosen so that its partial leakage flow is identical to that of each of the other gases in the mixture. The autocalibration means further include an electronic circuit 9 which to select the mass operates on the voltage accelerating ions formed in the mass spectrometer 2. The electronic circuit is controlled by a mass selector button 10. Finally, an electronic circuit 11 operates on the electronic current emitted by the cathode (filament or cold cathode) of the spectrometer to adjust the ionisation current (sensitivity adjustment). The parameters of this electronic circuit are varied by thumbwheels 12 on which the partial leakage flow of each of the gases in storage tank 6 is set (a single value is sufficient because the concentration of each gas is chosen so that its partial leakage flow is the same as that of the other gases).

To enable use of the leak detector, a valve 13 is disposed between the primary pump 4 and the secondary pump 3 and an inlet flange 14 adapted to be connected to an enclosure to be tested is connected to a primary pump 4 by a pipe 15 equipped with a pre-drain valve 16 and on the other hand to the spectrometer 2 via a pipe 17 equipped with an inlet valve 18.

With a device of the above kind, if the tracer gas is changed, it is sufficient to set the mass of the gas used on the button 10 during calibration.

If the leakage flow of each gas is not the same, the value of the leakage flow must also be modified on the thumbwheels 12. This is why it is preferable to choose for each gas in the storage tank 6 a concentration such that the partial leakage is the same for each gas.

With a device of the above kind, only one storage tank 6 is needed.

Figure 2:
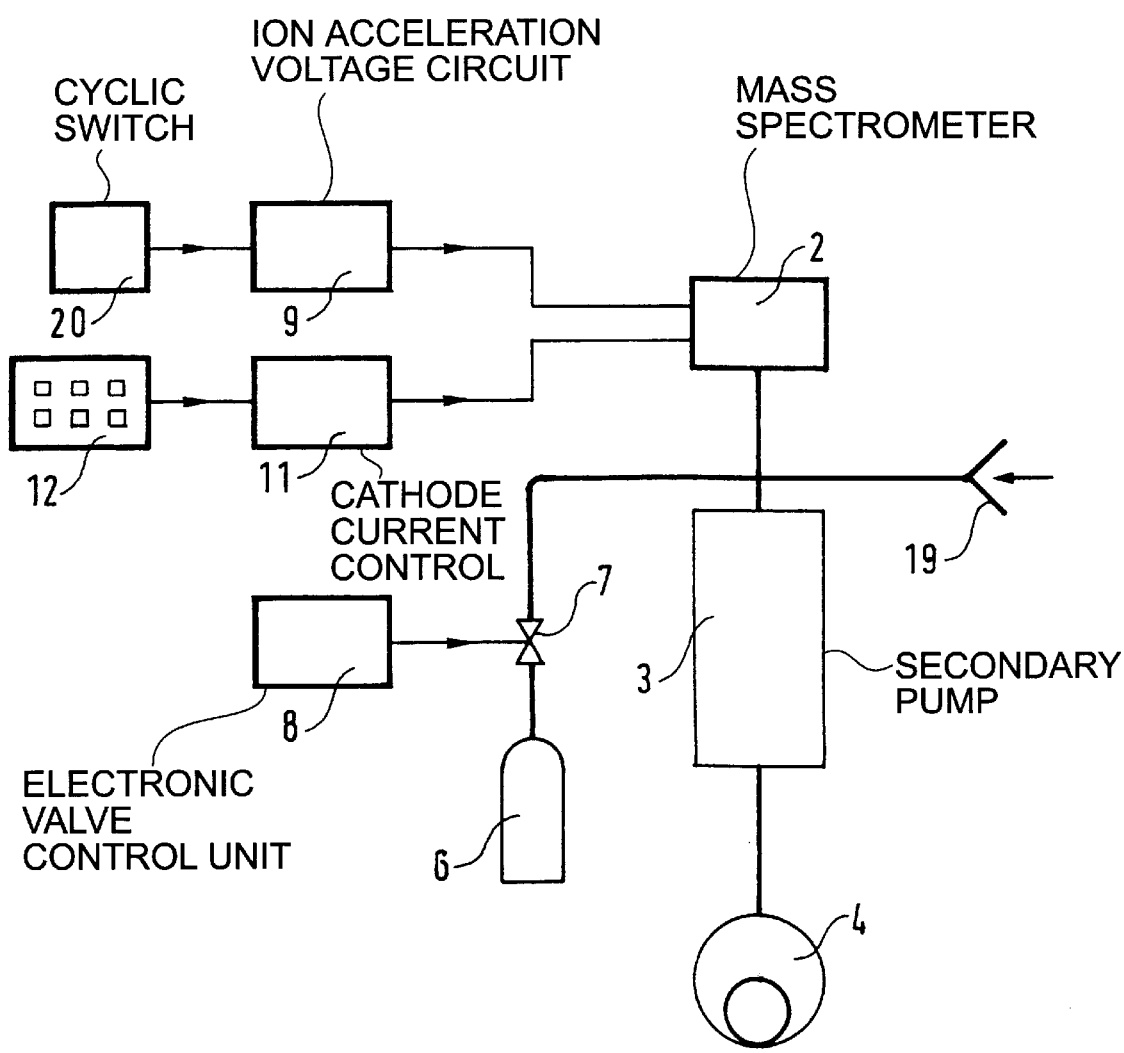
FIG. 2 is a diagram of a gas analyser in accordance with the invention used directly to analyse a flow of gas.

In FIG. 2, the gas analyser is used directly to analyse a gas mixture by mass spectrometry. The mixture is fed in at 19.

Here the storage tank 6 is therefore used to calibrate the analyser for each of the n gases that it contains using the known leakage value for each gas: as previously, an identical partial leakage is chosen for each gas by choosing suitable concentrations. In this application, the electronic circuit 9 includes a memory and the button 10 is replaced by a cyclic switch 20 scanning the masses of the gases contained in the storage tank 6. During calibration, the valve 7 is open and the setting of, the acceleration voltage corresponding to each mass is stored in the memory of the circuit 9. When analyzing a gas fed in at 19, with valve 7 closed, the switch 20 scans all the masses in succession and for each mass the circuit 9 sets the value of the acceleration voltage stored in memory for each mass during calibration.

What is claimed is:

1. A gas analyser comprising:

a pump unit; and an autocalibrator, wherein said gas analyser is connected to a storage tank having a calibrated leak and filled with a mixture of n gases having different masses, and a partial leakage flow of each of said n gases which through said calibrated leak is known.

2. The gas analyser according to claim 1, wherein the concentration of each of the n gases in the mixture is such that said partial leakage flow of each of the n gases through said calibrated leak is the same.

3. The gas analyser according to claim 1, wherein said gas analyser is part of a leak detector.

4. The gas analyser of claim 1, wherein said pump unit comprises a primary pump and a secondary pump.

5. The gas analyser of claim 4, further comprising:

a valve connecting said primary pump and said secondary pump; and an inlet flange coupled to the primary pump via a pipe equipped with a pre-drain valve, said inlet flange also coupled to a spectrometer.

6. The gas analyser of claim 1, said autocalibrator comprising:

a first electronic circuit, controlled by a mass selector, that selects the mass, said electronic circuit operating on voltage accelerating ions; and a second electronic circuit that operates on current emitted by a cathode to provide sensitivity adjustment.

7. The gas analyser of claim 6, wherein parameters of said second circuit are controlled by a thumbwheel.

8. The gas analyser of claim 1, further comprising:

a memory in an electronic circuit that sets a value of the acceleration voltage for each of said n gases; and a cyclic switch that successively scans the masses of gases in said storage tank.

* * * * *